United States Patent
Luna et al.

(10) Patent No.: US 10,456,179 B2
(45) Date of Patent: Oct. 29, 2019

(54) INTRAMEDULLARY ANKLE TECHNIQUE AND SYSTEM

(71) Applicant: Wright Medical Technology, Inc., Memphis, TN (US)

(72) Inventors: Ramon Luna, Arlington, TN (US); Matthew Talley, Collierville, TN (US); Christine M. Petteys, Bartlett, TN (US); David Reynolds, Fairport, NY (US); Paul Stemniski, Arlington, TN (US); Richard Obert, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 817 days.

(21) Appl. No.: 14/415,477

(22) PCT Filed: Mar. 14, 2014

(86) PCT No.: PCT/US2014/027193
§ 371 (c)(1),
(2) Date: Jan. 16, 2015

(87) PCT Pub. No.: WO2014/152308
PCT Pub. Date: Sep. 25, 2014

(65) Prior Publication Data
US 2015/0134071 A1 May 14, 2015

Related U.S. Application Data

(60) Provisional application No. 61/783,915, filed on Mar. 14, 2013.

(51) Int. Cl.
*A61B 17/58* (2006.01)
*A61B 17/88* (2006.01)
(Continued)

(52) U.S. Cl.
CPC .......... *A61B 17/7291* (2013.01); *A61B 17/15* (2013.01); *A61B 17/164* (2013.01);
(Continued)

(58) Field of Classification Search
CPC . A61B 17/7291; A61B 17/15; A61B 17/1624; A61B 17/164; A61B 17/1682;
(Continued)

(56) References Cited

U.S. PATENT DOCUMENTS 4,703,751 A   11/1987  Pohl
5,047,034 A * 9/1991  Sohngen ............ A61B 17/1725
                                                            606/87

(Continued)

FOREIGN PATENT DOCUMENTS

WO   2006099270 A2   9/2006

OTHER PUBLICATIONS

Extended European Search Report issued in connection with corresponding European patent application No. 14770967.9, dated Feb. 4, 2016, 7 pages.

(Continued)

*Primary Examiner* — Kevin T Truong
*Assistant Examiner* — Jessica Weiss
(74) *Attorney, Agent, or Firm* — Duane Morris LLP

(57) ABSTRACT

A prosthesis suited for orthopedic implantation comprising a modular intramedullary rod that provides intramedullary guidance and that supports an artificial joint surface that can articulate with another artificial joint surface in various ways. Intramedullary guidance systems and methods introduce some and/or all surgical tools and ankle prostheses components through the tibia, using minimal invasive exposure. The systems and methods align the talus and tibia for the installation of one or more ankle prostheses components, (Continued)

and also maintain that alignment during the installation using intramedullary guidance.

9 Claims, 8 Drawing Sheets

(51) Int. Cl.
    *A61B 17/90*     (2006.01)
    *A61B 17/72*     (2006.01)
    *A61F 2/42*     (2006.01)
    *A61B 17/15*     (2006.01)
    *A61B 17/16*     (2006.01)
    *A61B 17/92*     (2006.01)
    *A61B 17/17*     (2006.01)
    *A61F 2/30*     (2006.01)

(52) U.S. Cl.
    CPC ...... *A61B 17/1624* (2013.01); *A61B 17/1682* (2013.01); *A61B 17/1739* (2013.01); *A61B 17/72* (2013.01); *A61B 17/92* (2013.01); *A61F 2/4202* (2013.01); *A61B 17/1631* (2013.01); *A61B 17/1633* (2013.01); *A61B 17/1659* (2013.01); *A61B 17/1775* (2016.11); *A61F 2002/30329* (2013.01); *A61F 2002/30383* (2013.01); *A61F 2002/4205* (2013.01); *A61F 2002/4207* (2013.01)

(58) Field of Classification Search
    CPC ..... A61B 17/1739; A61B 17/72; A61B 17/92; A61F 2/4202; A61F 2002/30329; A61F 2002/30383; A61F 2002/4205; A61F 2002/4207
    USPC .............. 623/21.18; 606/87–89, 96–98, 104, 606/62–64, 67–68, 79–85
    See application file for complete search history.

(56) References Cited

U.S. PATENT DOCUMENTS

| | | | |
|---|---|---|---|
| 5,194,066 A | | 3/1993 | Van Zile |
| 5,499,984 A | | 3/1996 | Steiner et al. |
| 6,572,620 B1 * | | 6/2003 | Schon .................... A61B 17/72 606/60 |
| 6,699,293 B2 | | 3/2004 | White |
| 7,534,246 B2 | | 5/2009 | Reiley et al. |
| 8,337,503 B2 * | | 12/2012 | Lian ........................ A61B 17/15 606/87 |
| 2003/0187449 A1 * | | 10/2003 | McCleary .......... A61B 17/1668 606/80 |
| 2005/0124995 A1 * | | 6/2005 | Reiley ................... A61B 17/15 606/62 |
| 2006/0106393 A1 * | | 5/2006 | Huebner .............. A61B 17/164 606/80 |
| 2006/0229730 A1 * | | 10/2006 | Railey ................... A61B 17/15 623/21.18 |
| 2009/0306664 A1 * | | 12/2009 | Teeny .................. A61B 17/725 606/64 |
| 2010/0004743 A1 | | 1/2010 | Strzepa |
| 2010/0262150 A1 | | 10/2010 | Lian |
| 2010/0319993 A1 | | 12/2010 | Bhome et al. |
| 2012/0271314 A1 | | 10/2012 | Stemniski et al. |
| 2013/0046311 A1 | | 2/2013 | Blake et al. |
| 2013/0046313 A1 | | 2/2013 | Lian |
| 2013/0053856 A1 * | | 2/2013 | Penenberg ......... A61B 17/1659 606/91 |

OTHER PUBLICATIONS

Communication issued in connection with corresponding European patent application No. 14770967.9, dated Nov. 7, 2016, 4 pages.
Re-Examination Report issued in connection with corresponding Australian patent application No. 2014239941, dated Nov. 23, 2016, 4 pages.s.
International Search Report issued for corresponding International Patent Application No. PCT/US2014/027193, dated Jul. 1, 2014, 4 pages.
English Translation of the First Office Action issued by the Examiner in connection with corresponding Chinese Application No. 201480002524.2, dated Dec. 1, 2015, 4 pages.
International Preliminary Report on Patentability issued for International Application No. PCT/US2014/027913, dated Sep. 24, 2015, 7 pages.
Office Action issued in connection with corresponding Canadian patent application No. 2,967,478, dated Mar. 27, 2018, 3 pages.
Extended Search Report issued in connection with corresponding European patent application No. 18181350.2, dated Oct. 19, 2018, 8 pages.

* cited by examiner

US 10,456,179 B2

INTRAMEDULLARY ANKLE TECHNIQUE AND SYSTEM

CROSS-REFERENCE TO RELATED APPLICATIONS

This application claims priority to U.S. Provisional Patent Application No. 61/783,915, filed Mar. 14, 2013, the entirety of which is incorporated by reference herein.

FIELD OF THE INVENTION

The invention relates to ankle replacement prostheses and systems, as well as associated surgical instruments and procedures.

BACKGROUND OF THE INVENTION

Until the early to mid-1970's, patients with injured or diseased ankle joints commonly resulting from rheumatism, or degenerative or traumatic arthritis, had few options when their ankle joints failed. The most common procedure to help these patients regain some use of their ankle was obliteration of the joint by fusion, a procedure that is still commonly used today. Fusion, however, renders the ankle stiff and generally immobile relative to the lower leg, resulting in limited use and additional stresses on the knee and hip joints.

Total ankle prosthesis have been used since at least as early as 1969. The medical community recognized that such ankle replacement led to largely increased use of the ankle joint because the replacement permitted ankle ranges of motion which generally attempted to mimic the natural human joint. Since that time, ankle replacement prostheses have become increasingly common in use and improved in design. However, less invasive surgical methods with improved healing and decreased failure rates are desirable.

SUMMARY OF THE INVENTION

Figure 1:
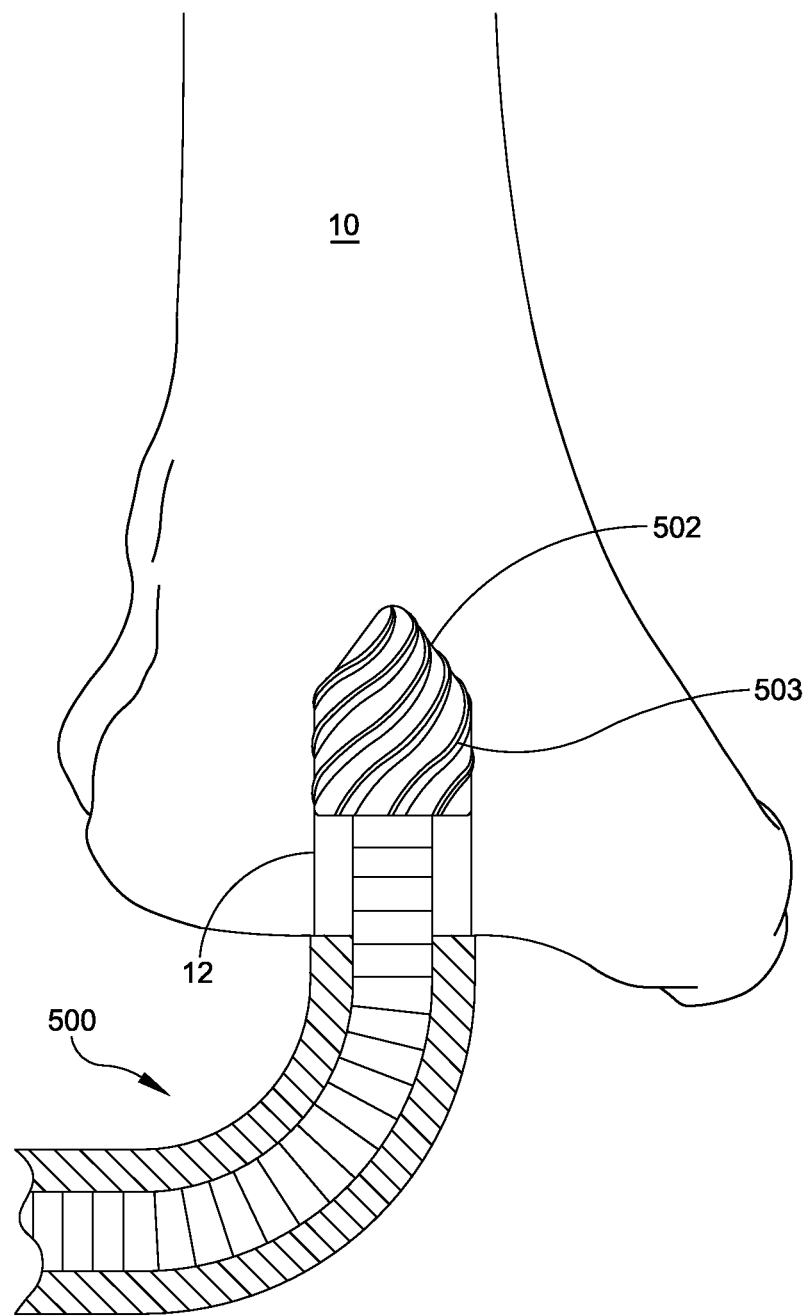
FIG. 1 illustrates one example of a curved reamer reaming an intramedullary cavity in a tibia in accordance with some embodiments.

In one embodiment, an intramedullary rod is provided that includes a plurality of modular components sized and configured to be disposed in an intramedullary canal. The modular components are configured to be interconnected with one another in situ, with the distal-most modular component is a base component configured to engage an alignment guide.

A system is provided for intramedullary guidance to implant an ankle prosthesis that includes a first tool sized and configured to form a passage between a tibia and a talus and a second tool sized and configured to create an intramedullary canal in a distal end of the tibia. A plurality of modular tibial rod components are provided, sized, and configured to be disposed in the intramedullary canal and connected to each other in situ to form a single tibial rod component. A base modular component located on a distal end of a tibial rod component is configured to engage an alignment guide. The alignment guide is configured to translate coronal, transverse, and sagittal adjustments from the alignment guide to a cutting guide.

In one method according to the invention, a plurality of modular components are inserted into an intramedullary canal, and connected in situ to form a single intramedullary rod component, with the distal end of the intramedullary rod component being connected to an alignment guide.

In a further method of implanting an ankle prosthesis system a passage is formed between a tibia and a talus so as to define an intramedullary canal in a distal end of a tibial shaft with a flexible reaming tool. A plurality of modular rod components are introduced inferiorly through the intramedullary canal into the tibial shaft so as to interconnect the modular rod components to form a single tibial rod component thereby allowing a modular tibial base component to be coupled to a distal-most end of the tibial rod component. An alignment guide is coupled to the tibial base component using the alignment guide to translate adjustments to a cutting guide.

DETAILED DESCRIPTION OF THE PREFERRED EMBODIMENTS

This description of preferred embodiments is intended to be read in connection with the accompanying drawings, which are to be considered part of the entire written description of this invention. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

This description is divided into logical sections for ease of disclosure. Section I provides structural descriptions of representative embodiments of a modular intramedullary rod component of a total ankle replacement system and exemplary devices that have the desired form, fit, and function. Section II provides descriptions of representative embodiments of systems, methods, and techniques useful for the implantation of total ankle replacement systems using intramedullary guidance and devices to achieve the desired form, fit, and function.

Although the disclosure hereof is detailed and exact to enable those of ordinary skill in the art to practice the invention, the physical embodiments herein disclosed are merely examples. While the preferred embodiments have been described, the details may be changed without departing from the spirit and scope of the present invention, which is defined by the claims.

I. Modular Intramedullary Rod Component

Figure 10:
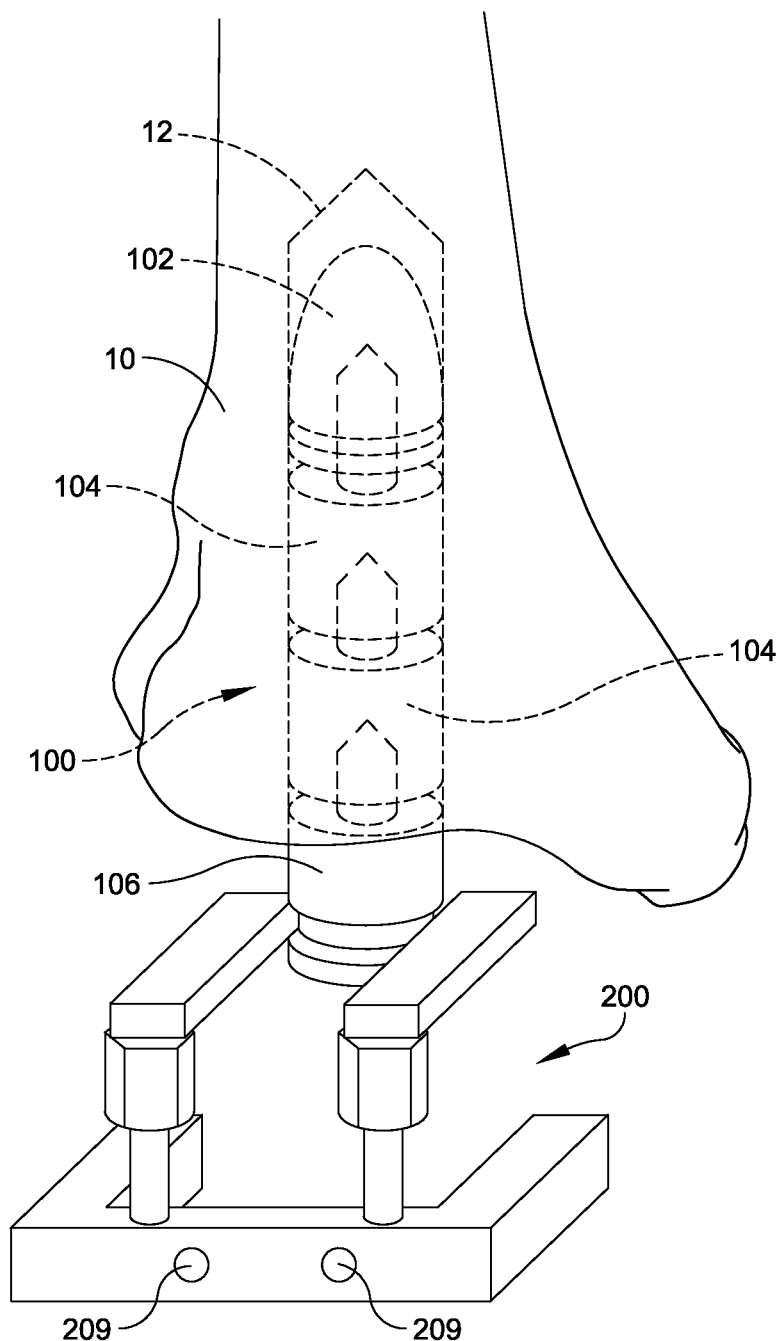
FIG. 10 illustrates a plurality of intramedullary rod components disposed within an intramedullary canal and coupled to a varus/valgus and plantar/dorsi flexion alignment guide in accordance with some embodiments.

Two or more modular components may form an intramedullary rod component suitable for use in any surgical procedure in which a rod is used for intramedullary guidance of surgical tools or fixation of an implant, whether it is a total joint implant, fusion (arthrodesis) implant, osteotomy fixation implant, or fracture fixation implant. As illustrated in FIG. 10, for example, a rod component 100 includes a top (i.e., superior) modular component 102, one or more optional mid-modular components 104, and a base (i.e., inferior) modular component 106. Top component 102 is preferably convex or domed to facilitate advancement of rod 100 in the direction of top component 102 within an intramedullary canal 12 within tibia 10. The modular component configuration is ideally suited for securing prosthetic components together in a minimally invasive procedure. This configuration is also ideally suited for minimally invasive surgeries in which a small surgical opening is used to install relatively larger prosthetic components.

Two or more of modular components 102, 104, 106 may be sequentially connected to one another, in situ, to form a single intramedullary rod assembly 100. For example, top modular component 102 may be joined with a base modular component 106. Alternatively, one or more mid-modular components 104 may be placed between top 102 and base 106 modular components to form an intramedullary rod 100 of a desired length. Modular components 102, 104, 106 may be attached to one another by a variety of fixation structure, e.g., morse tapers, complementary threaded structures, or bayonet mounts of the type known in the art.

Thus, a plurality of modular components 102, 104, 106 may be assembled so as to form a single intramedullary rod component 100. Intramedullary rod component 100 may be positioned and fixed within a tibia 10 with bone cement, hydroxyapatite, a ground bone composition, screws, or a combination thereof, or any other fixation materials suitable for prosthetic surgery. For example, a modular intramedullary rod 100 placed in a tibial intramedullary canal may be fixed to the tibia with screws. If screws are used, they may extend anteriorly, posteriorly, medially, laterally and/or at oblique angles, or any combination thereof.

One or more of modular components 102, 104, 106 may include a configuration for engagement with a driver or other tool to facilitate advancement of the component within bone and/or to torque one component into an adjacent component. Similarly, one or more of modular components 102, 104, 106 may include a second configuration for engagement with a wrench or other tool to grasp or otherwise secure the component during installation.

Each modular component 102, 104, 106 is desirably sized and configured to be individually installed through a small incision, e.g., a small anterior opening in the ankle, and through a passage between a tibia and a talus (which has been formed in advance). In this way, individual modular components 102, 104, 106 may be sequentially joined together, in situ, e.g., within a reamed intramedullary canal 12 within tibia 10 and progressively advanced up the intramedullary canal 12, top modular component 102 first.

Figure 11:
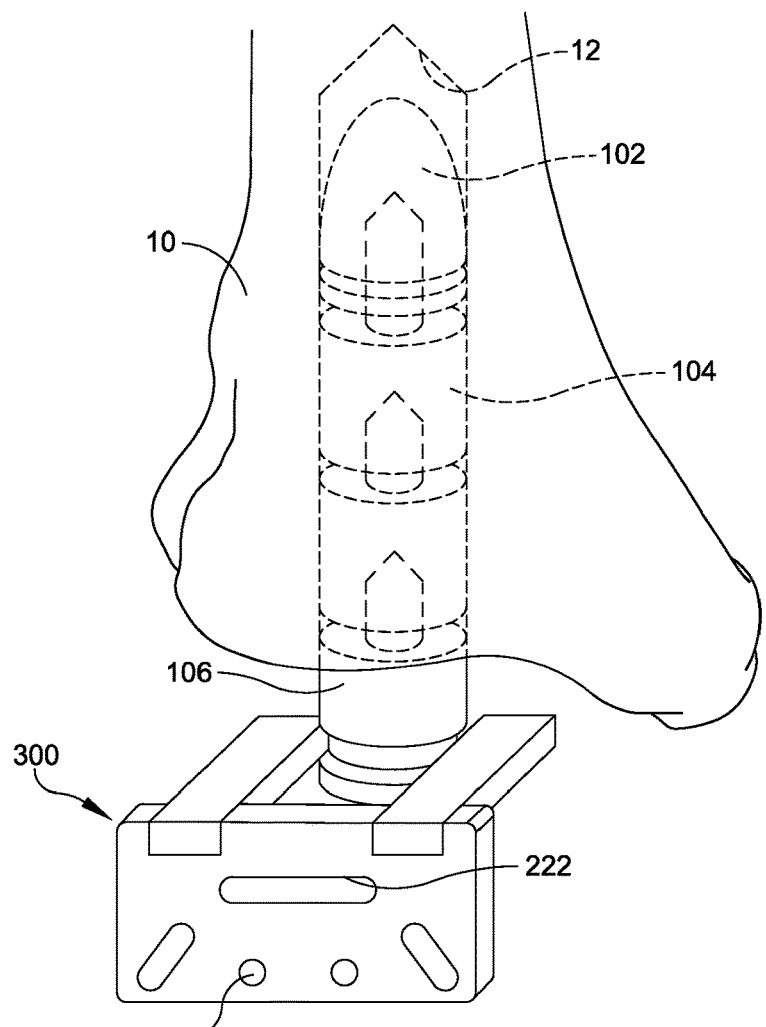
FIG. 11 illustrates a plurality of intramedullary rod components disposed within an intramedullary canal and coupled to a tibial cut guide in accordance with some embodiments.
Figure 12:
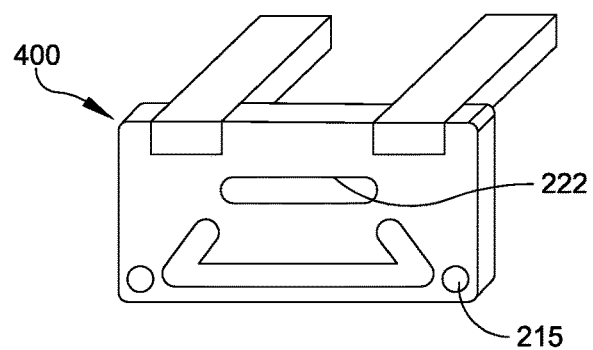
FIG. 12 illustrates one example of a tibia and talar cut guide in accordance with some embodiments.

The last or base component 106 is sized and configured to attach to an alignment guide 200. Alignment guide 200 is configured to make coronal, transverse, or sagittal adjustments and, to aid in preparing a joint to receive an ankle replacement prosthesis. Alignment guide 200 may comprise one or more pins, such as Steinmann pins, to translate the coronal, transverse, and/or sagittal adjustments to a cutting guide 300, 400 (FIGS. 11 and 12). Also, a cutting guide 300 may be configured to aid in making a cut in tibia 10 in order to prepare it for receiving a tibial component of an ankle replacement prosthesis in accordance with embodiments of the invention. Cutting guide 400 may be configured to aid in cutting tibia 10 and/or talus 20 to prepare the bones to receive a total ankle prosthesis. Once the cuts have been made to the appropriate portions of tibia 10 or talus 20, and using intramedullary rod component 100 to provide guidance of the tibial and/or talar cuts that are to be made (FIG. 13), modular rod component 100 may be disengaged from alignment guide 300, 400. Base component 106 is configured to then attach to a tibial component of an ankle prosthesis that would comprise the upper half of an ankle prosthesis.

Modular components 102, 104, 106 may be made of any material suitable for forming a total joint or materials suitable for use in the prosthetic arts including, but not limited to, metals, ceramics, titanium, titanium-alloys, tantalum, chrome cobalt, surgical steel, polyethylene, absorbable polymer, or any other total joint replacement metal and/or ceramic, bony in-growth surface, sintered glass, artificial bone, any uncemented metal or ceramic surface, or a combination thereof. Modular components 102, 104, 106 may further be covered with one or more coatings such as antimicrobial, antithrombotic, and osteoinductive agents, or a combination thereof. These agents may further be carried in a biodegradable carrier material with which the pores of tibial rod component may be impregnated.

Modular intramedullary rod 100 configuration not only permits installation using minimally-invasive surgical procedures, but provides a means to install long fixation members or rods that might not be achievable if they were constructed of a single piece. While the long or extended length of the modular intramedullary rod is particularly well-suited for use in the tibia, the modular rod could be used in other long bones or, in the talus as well.

II. Intramedullary Guidance System and Technique

Proper overall alignment of the total ankle prosthesis and improved long term results are achieved with embodiments of the present invention. Desirably, the ankle replacement prosthesis is installed using minimally invasive intramedullary guidance. Intramedullary guidance is established with respect to the major axis of the tibia by minimally invasive access through a passage formed between tibia 10 and talus 20, via an incision in the anterior portion of the ankle, and through the tibial shaft. Intramedullary guidance along the axis of the tibia makes it possible to make properly oriented bone cuts of the talus and tibia through an anterior access incision to the ankle joint. Using installation tools, systems, and techniques that incorporate intramedullary guidance, the total ankle system prosthesis can be installed in desired alignment and orientation with all the natural axes of the native ankle joint it replaces. These natural axes include the anterior to posterior axis (Y-horizontal axis) of rotation of the ankle joint, the natural medial-to-lateral axis (X-horizontal axis) of rotation of the ankle joint, and the natural superior-to-inferior axis (Z-vertical axis) of alignment of the ankle joint with the major axis of the tibia.

Among the benefits achieved by the invention is establishing and maintaining proper alignment of the anterior to posterior axis (Y-horizontal axis) of rotation, so that the ankle replacement prosthesis establishes and maintains the desired degree of plantar-dorsi ("up and down") flexion of the foot. Further, by establishing and maintaining proper alignment of the natural medial-to-lateral axis (X-horizontal axis) of rotation, the prosthesis establishes and maintains the desired degree of inversion/eversion ("in and out") rotation of the foot. In addition, by establishing and maintaining proper alignment of the natural superior-to-inferior axis (Z-vertical axis) of alignment of the ankle joint with the long axis of the tibia, the prosthesis is accurately oriented with respect to the central tibial axis of the leg, so that intramedullary support can be achieved by inferior drilling of the tibia using fluoroscopic guidance.

A. Boring the Tibia for the Modular Intramedullary Rod Component

A physician makes an incision on an anterior portion of an ankle joint. A first tool, e.g. a guide pin, may be used to establish or to create a passage between the tibia and the talus bones. The passage provides anterior access to a distal end of the tibial shaft so that an intramedullary canal may be formed. A second tool is provided, such as a flexible intramedullary reamer 500 (FIG. 1) for the purpose of establishing an intramedullary canal 12 within the tibia 10. Canal 12 is configured to receive modular tibial rod components 102, 104, 106, making use of the anterior access through the cleared passage between tibia 10 and talus 20. Reamer 500 advantageously includes a bullet-shaped, i.e., parabolic or rounded conical, nose 502 having cutting flutes 503 on an outer surface, and that fits within the previously formed passage between the tibia and the talus. Entering the passage, reamer 500 forms an intramedullary tibial canal 12. A depth mark can be noted on the reamer so that the tibia is reamed to a predetermined depth as deemed appropriate by the physician. The physician may retract reamer 500 through the anterior passage previously formed between tibia 10 and talus 20, via intramedullary canal 12, for installation of the modular intramedullary rod 100.

Figure 2:
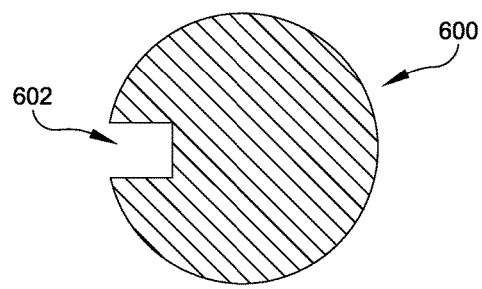
FIG. 2 is a plan view of one example of a broach in accordance with some embodiments.
Figure 3:
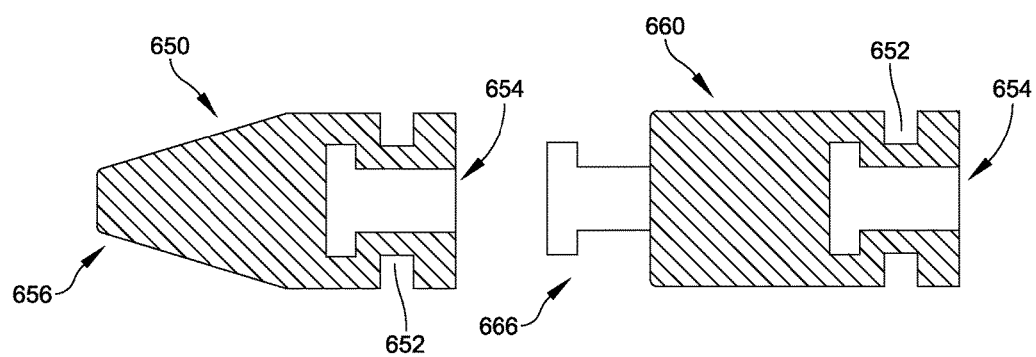
FIG. 3 is a cross-sectional view of one example of different modular broach components in accordance with some embodiments.

In some embodiments, one or more broaches 600 may be arranged and used to create intramedullary canal 12. For example, FIGS. 2-6 illustrate examples of modular broach components 650 that may be coupled together and thereafter forced into the intramedullary canal 12 of a tibia 10 so as to selectively enlarge the diameter of the canal. FIG. 2 illustrates a dove-tail 602 configured to allow the alignment of the modular broach components. As illustrated in FIG. 3, broach components 650, 660 include a groove at one end that is sized and configured to be coupled to a handle or to engage a complementary structure of another broach component so as to couple the two broach components together. The exterior surface of broach components 650, 660 respectively define circumferential groove 652 suitable for being engaged by a holding tool. Broach component 650 tapers at a first end 656 and includes cutting flutes 503 that are suitable for cutting bone. An opening 654 is defined at the opposite end of broaching component 650 and configured to engage a coupling structure 666, e.g., a "T-shaped post, extending from an end of broach component 660. Broach component 660 also defines an opening configured to engage an engagement structure 666 of another broach component 660.

Figure 4:
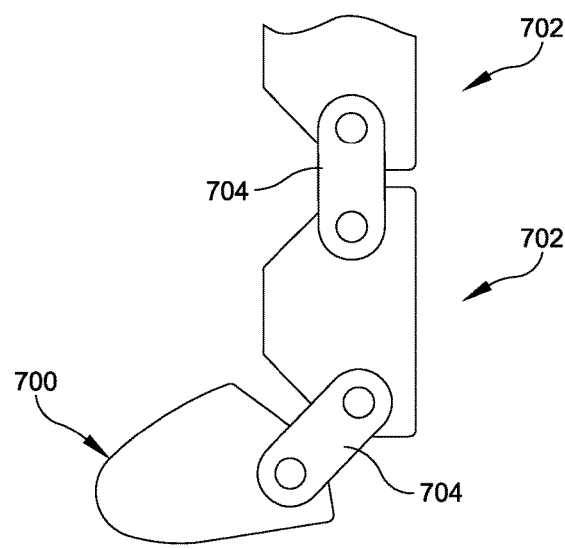
FIG. 4 illustrates a pair of angled broach components coupled together via a hinge in accordance with some embodiments.
Figure 5:
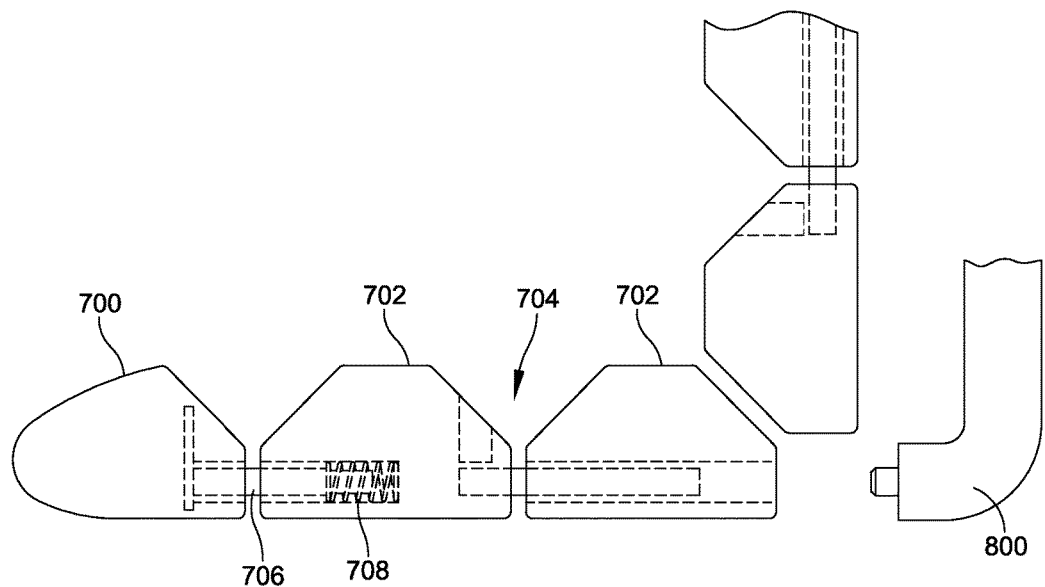
FIG. 5 illustrates a plurality of broach components hinged together in accordance with some embodiments.
Figure 6:
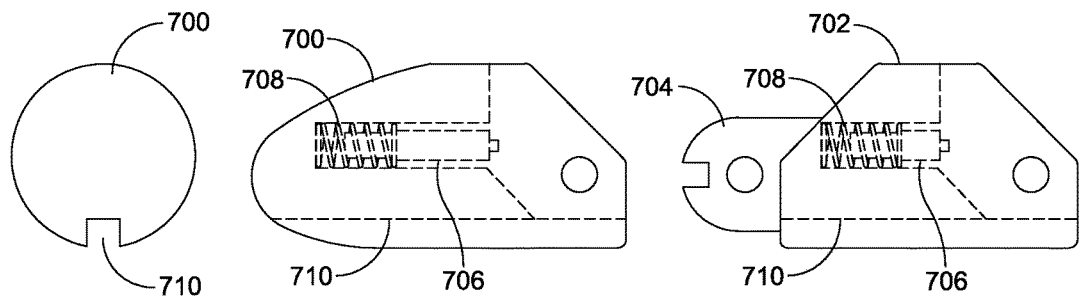
FIG. 6 provides various view of broach segments in accordance with some embodiments.

Referring to FIGS. 4, 5, and 6, broach components 700, 702 may be hingedly coupled to one another by a plurality of hinges 704. In some embodiments and as best seen in FIG. 5, a spring-loaded dowel pin 706 (i.e., a dowel pin 706 biased by a spring 708 or other biasing member) is configured to align two broach components/segments 700, 702. When dowel pin 706 is retracted by, e.g., inserting a wedged tip into an extractor hole, adjacent segments 700, 702 that are coupled together are able to be bent or pivot relative to one another. When dowel pin 706 is engaged, broach components 700, 702 are locked relative to one another. Also, an impactor tip 800 is configured to be connected to a broach 700, 702. As best seen in FIG. 6, broaches 700, 702 may define a groove 710 sized and configured to receive a rail of a tibial stem guide therein.

Figure 8:
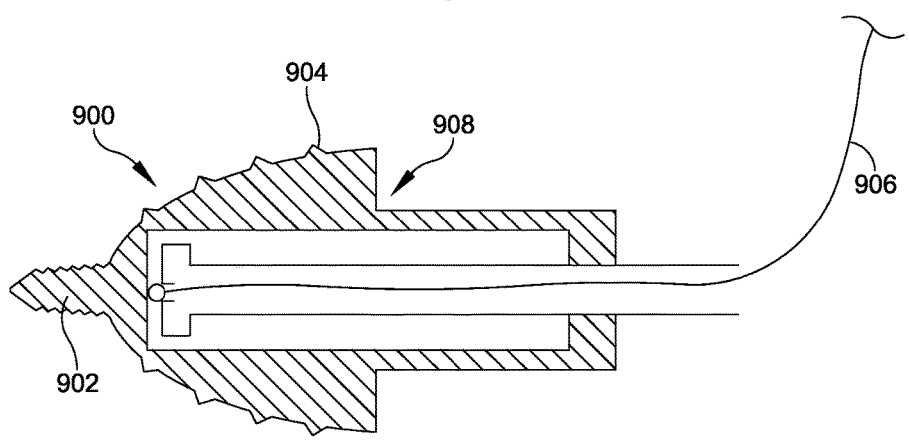
FIG. 8 is a cross-sectional view of one example of a self-advancing reamer in accordance with some embodiments.
Figure 9:
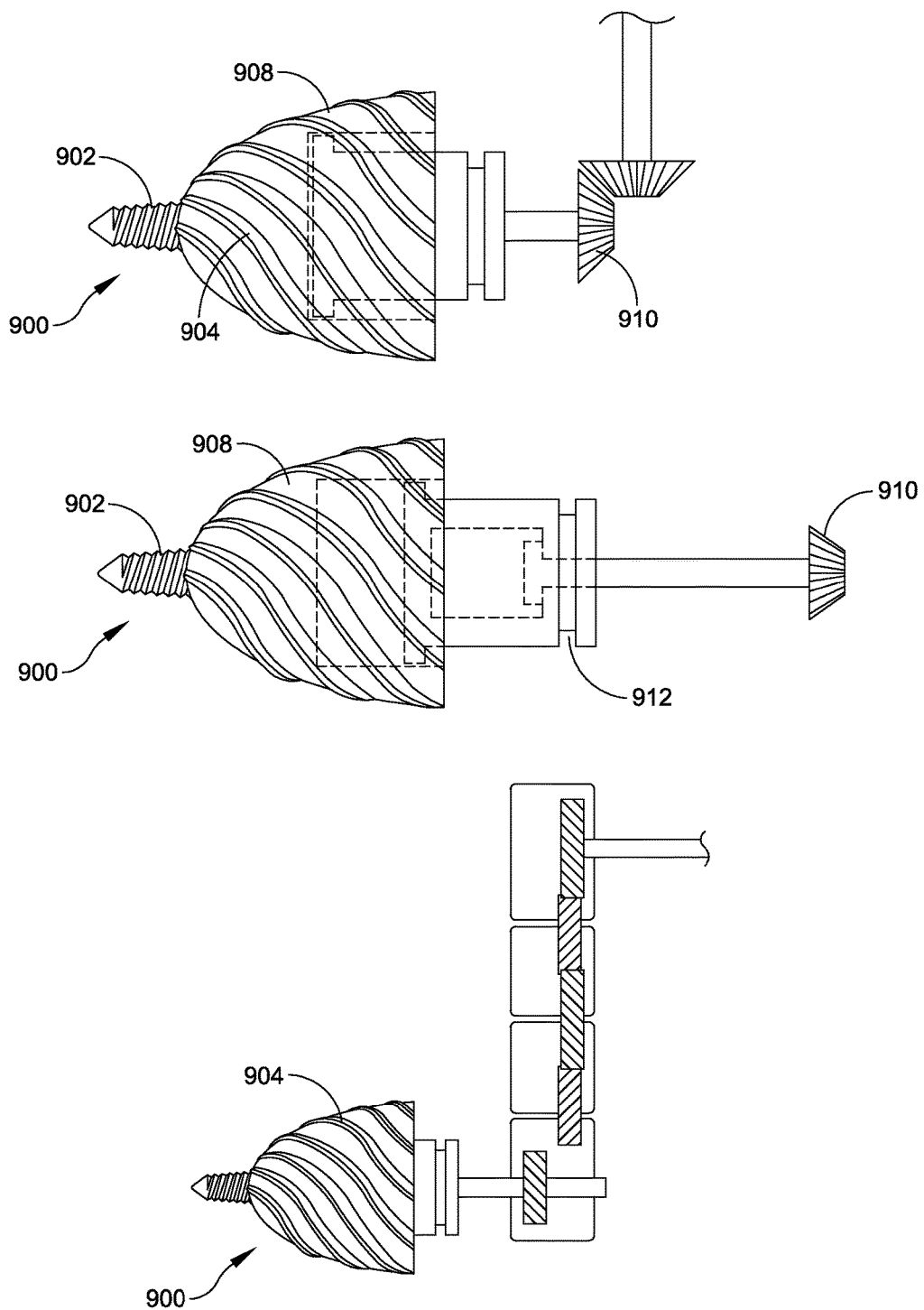
FIG. 9 illustrates various views of examples of angled reamers in accordance with some embodiments.

FIGS. 8 and 9 illustrate examples of self-advancing reamers 900. In FIG. 8, reamer 900 includes a threaded tip 902 that pulls or otherwise advances reamer 900 into bone. Reamer 900 also includes flutes 904 configured to pull the reamer through the bone as reamer 900 cuts the bone. In some embodiments, a retrieval wire 906 is coupled to reamer body 908 and is configured to be pulled by a surgeon or other medical professional to retrieve the reamer from an intramedullary channel. As shown in FIG. 9, a self-advancing reamer 900 may include a beveled gear assembly 910 that is slidably coupled to reamer body 908 such that reamer body 908 can be advanced into an intramedullary canal with the reamer gearing remaining in position (although allowed to rotate). In some embodiments, a circumferential groove 912 is provided that is sized and configured to be coupled to other guide structures, which allows beveled gear assembly 910 to rotate while being held in a fixed position as reamer body 908 advances axially within the bone. In some embodiments, the reamer is driven by a gear chain disposed within reamer body 908 that is configured to interface with an alignment guide for holding the reamer step perpendicular to the resection.

Figure 7:
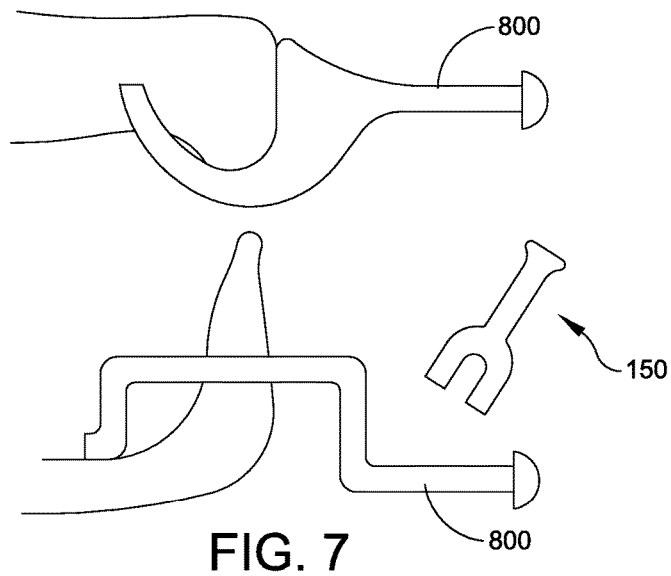
FIG. 7 illustrates a handle in accordance with some embodiments.

FIG. 7 illustrates one example of handle 150 configured to allow slap-hammer 800 to assist with the extraction of broach segments and can also be used for revision implant extraction. In some embodiments, the external broach handle 150 includes a modular tip configured to be coupled to modular or hinged broaches and prosthesis components (e.g., stem and/or trays) for impacting the prosthesis within an intramedullary cavity.

B. Installing the Intramedullary Rod Component

Once intramedullary canal 12 has been formed within the distal tibia, it is ready to receive the multi-component, modular intramedullary rod 102, 104, 106 as illustrated in FIGS. 10 and 11. In this installation sequence, as in previously described sequences of the installation, installation of the modular intramedullary rod 102, 104, 106 takes advantage of the anterior access incision provided in the cleared joint passage between the tibia and talus. The physician inserts the top tibial modular component 102 into the joint space through the previously formed anterior passage. The assembly tool engages top modular component 102, by gripping the top modular component. Top modular component 102 is advanced partially up into the preformed tibial canal.

A mid-modular component 104 is inserted through the same anterior incision. A driver is configured to engage mid-modular component 104, with a tool engaging top modular component 102 to keep it from rotating, the physician twists the driver to torque the threaded male end of mid-modular component 104 into the threaded female end of top modular component 102. This joins the top and mid modular components 102,104. Once tightened, the wrench is switched from top modular component 102 to mid-modular component 104. The physician axially advances the driver to push top modular component 102 beyond the confines of the cleared joint space and up into the tibial canal.

C. Making Bony Cuts in the Talus and Tibia

Figure 13:
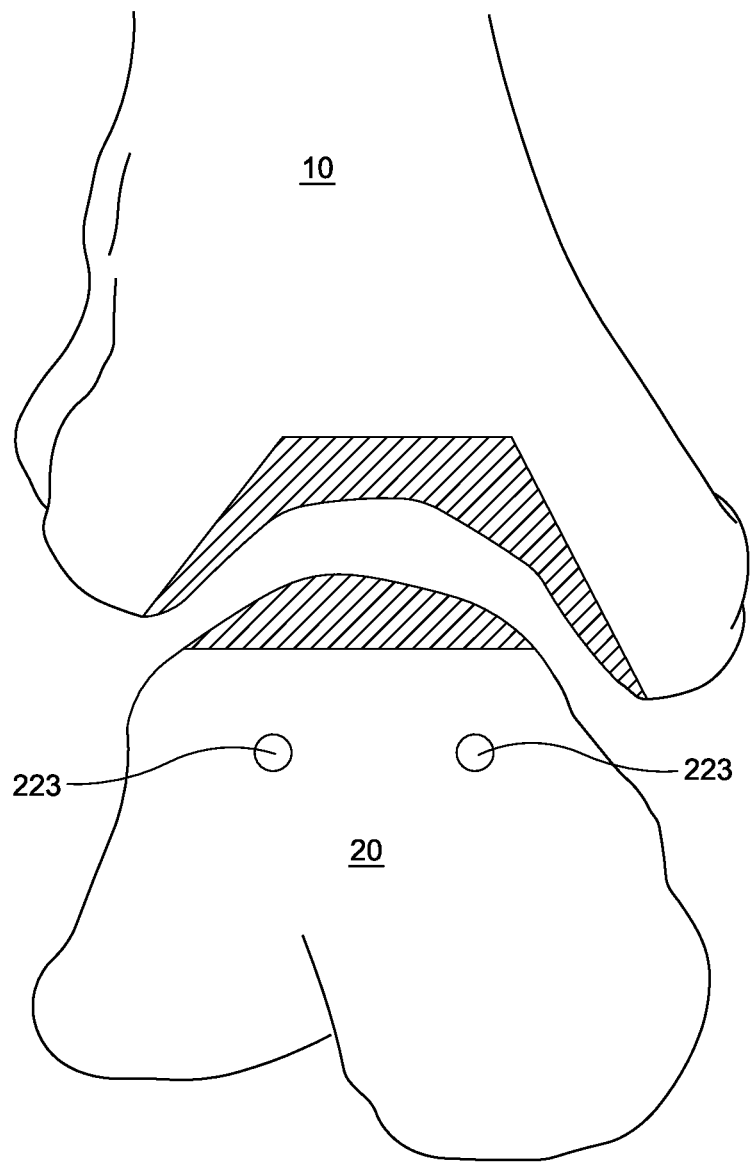
FIG. 13 illustrates one example of tibia and talar cuts having been made in accordance with some embodiments.

In the representative embodiments, base modular component 106 of the intramedullary rod is sized and configured to engage alignment guide 200 (FIG. 10) which allows for coronal, transverse, and sagittal adjustments. Additionally, alignment guide 200 may comprise one or more pin holes 209 configured for receiving Steinmann pins that may be used to translate the coronal, transverse and/or sagittal adjustments from alignment guide 200 to cutting guide 300. Cutting guide fixtures 300, 400 (FIGS. 11 and 12) may be configured to aid in making a bony cut in the tibia. Alternatively, cutting guide 300 may be configured to aid in making bony cuts in both the tibia and the talus. Cutting guide fixtures 300, 400 may be installed and stabilized over the ankle joint in an anterior, posterior, or lateral position relative to the ankle joint. Cutting guide fixtures 300, 400 may be secured either directly to intramedullary rod 100 or to underlying frame 200 to which the alignment guide is also attached (FIGS. 11 and 12). Cutting guide fixtures 300, 400 may include a superior bone cutting blade guide and an inferior bone cutting blade guide. The cutting guide fixture also includes apertures 215 for receiving fixation pins adjacent the superior and inferior blade guides 222. In a representative embodiment, the pins can comprise Steinmann pins. A pair of the pins are positioned in tibia 10, adjacent to a superior blade guide and another pair of pins are positioned in passageways 223 located in talus 20, adjacent an inferior blade guide so as to resect those portions of the distal tibia and proximal talus as schematically illustrated in FIG. 13. Modular intramedullary rod 100 component helps to ensure that the joint components maintain the correct alignment relative to one another so that the resulting cuts are more accurately positioned. Fluoroscopy may be used to aid in making the bony cuts.

D. System and Technique for Installing a Total Ankle Prosthesis

After the bony cuts have been made, the fixture and pins may be disengaged from the base modular component. Loose bone pieces are removed and the cleared joint space irrigated. The cleared joint space and the anterior passage provide for the insertion of other installation tools and the components of a total ankle replacement prosthesis. For example, an artificial tibial joint surface may be coupled to the distal end of modular intramedullary rod component 106. Further, an artificial talar joint surface may be fixed to the talus for articulation with the artificial tibial joint surface.

Other embodiments and uses of the apparatuses, systems, and methods described herein will be apparent to those of ordinary skilled in the art from consideration of the specification and practice of the disclosed methods. The specification should be considered exemplary only with the true scope and spirit of the apparatuses, systems, and methods indicated by the following claims. As will be easily understood by those of ordinary skill in the art, variations and modifications of each of the disclosed embodiments can be easily made within the scope of the disclosed apparatuses, systems, and methods as defined by the following claims.

What is claimed is:

1. A system for providing intramedullary guidance to implant an ankle prosthesis, comprising:
   a first tool sized and configured to form a passage between a tibia and a talus,
   a second tool sized and configured to create an intramedullary canal in a distal end of said tibia,
   a plurality of modular tibial rod components sized and configured to be disposed in said intramedullary canal and connected to each other in situ to form a single tibial rod component,
   a base modular component on a distal end of said single tibial rod component,
   an alignment guide configured to attach to said base modular component, and
   a cutting guide including at least one aperture configured to guide an instrument in making a tibial cut;
   wherein said alignment guide is configured to translate coronal, transverse, and sagittal adjustments from the alignment guide to the cutting guide; and
   further comprising at least one broach comprising a circumferential groove configured to engage a holding tool, the circumferential groove extending into an exterior surface of the at least one broach, wherein the at least one broach comprises a first broach component configured to be hingedly coupled to a second broach component to allow alignment of the first broach component and the second broach component such that the first broach component and the second broach component can be inserted into the intramedullary canal to enlarge the diameter of the intramedullary canal.

2. The system of claim 1, wherein the first tool includes a guide pin.

3. The system of claim 1, wherein the cutting guide is also configured to aid in making a talar cut.

4. The system of claim 1, wherein the cutting guide is configured to be attached to said base modular component.

5. The system of claim 1, wherein the second tool comprises an intramedullary reaming device.

6. The system of claim 5, wherein the intramedullary reaming device comprises a flexible reaming device.

7. The system of claim 5, wherein the intramedullary reaming device includes a threaded tip configured to advance the intramedullary reaming device into bone as the intramedullary reaming device is rotated.

8. A method of implanting an ankle prosthesis system using the system of claim 1, comprising:
   forming a passage between a tibia and a talus;

forming an intramedullary canal into a distal end of a tibial shaft with a flexible reaming device, passing a plurality of modular rod components inferiorly through the intramedullary canal into the tibial shaft, connecting said modular rod components in situ to form a single tibial rod component in said intramedullary canal, coupling a modular tibial base component to a distal-most end of the tibial rod component, coupling an alignment guide to said tibial base component, coupling a cutting guide to said alignment guide, said cutting guide including at least one aperture configured to guide an instrument in making a tibial cut; and using said alignment guide to translate coronal, transverse, and sagittal adjustments from said alignment guide to said cutting guide.

9. A system for providing intramedullary guidance to implant an ankle prosthesis, comprising:

a first tool sized and configured to form a passage between a tibia and a talus, a second tool sized and configured to create an intramedullary canal in a distal end of said tibia, a plurality of modular tibial rod components sized and configured to be disposed in said intramedullary canal and connected to each other in situ to form a single tibial rod component, a base modular component on a distal end of said single tibial rod component, an alignment guide configured to attach to said base modular component, and a cutting guide including at least one aperture configured to guide an instrument in making a tibial cut;

wherein said alignment guide is configured to translate coronal, transverse, and sagittal adjustments from the alignment guide to the cutting guide; and further comprising at least one broach wherein the at least one broach comprises a first broach component configured to be hingedly coupled to a second broach component, and further comprising a dowel pin disposed in an aperture of one of the first broach component and the second broach component, wherein the dowel pin is configured to move from an engaged position to a disengaged position, and wherein when the dowel pin is in the engaged position the first broach component and the second broach component are locked relative to one another and when the dowel pin is in the disengaged position the first broach component and the second broach component can pivot relative to one another.

* * * * *